United States Patent [19]

King

[11] Patent Number: 5,766,932
[45] Date of Patent: Jun. 16, 1998

[54] PROCESS FOR PREPARING N-ACETYL(L)-4-CYANOPHENYLALANINE FROM A MIXTURE OF THE CORRESPONDING D,L ETHYL ESTERS USING SUBTILISIN

[75] Inventor: Chi-Hsin R. King, Taipei, Taiwan

[73] Assignee: Hoechst Marion Roussel, Inc., Cincinnati, Ohio

[21] Appl. No.: 767,760

[22] Filed: Dec. 17, 1996

Related U.S. Application Data

[60] Provisional application No. 60/080,231, Dec. 20, 1995.
[51] Int. Cl.⁶ .................... C12P 13/22; C12P 41/00
[52] U.S. Cl. ........................... 435/280; 455/108
[58] Field of Search ........................ 435/280, 108

[56] References Cited

U.S. PATENT DOCUMENTS 4,262,092  4/1981  Bauer ........................ 435/280

FOREIGN PATENT DOCUMENTS

| 0508220 | 3/1992 | European Pat. Off. . |
| 0513675 | 11/1992 | European Pat. Off. . |
| 155-954 | 2/1981 | German Dem. Rep. . |
| 3733506 | 4/1989 | Germany . |
| 4115468 | 11/1992 | Germany . |
| 95/29189 | 11/1995 | WIPO . |

OTHER PUBLICATIONS

Kise et al., Biotech. Lett. 13(5):317–322 (1991).
Jendralla, et al., Tetrahedron 51(44), pp. 12047–68 (1995).
Folkers, Karl et al., Int. J. Peptide Protein Res., vol. 24, pp. 197–200 (1984).
Solladié–Cavallo A. et al., Tetrahedron:Asymmetry, vol. 5, No. 8, pp. 1621–1626 (1994).
Pattabiraman et al., Biochem J., vol. 126, pp. 645–657 (1972).
Pattabiraman et al., Biochem J., vol. 126, pp. 659–665 (1972).
P. Narasimhja Rao et al., Int. J. Peptide Protein Res., vol. 29, pp. 118–125 (1987).
Chenevert, et al., Can. J. Chem., vol. 68, pp. 960–963 (1990).
Faber K., Biotransformations in Organic Chemistry Springer–Verlag, pp. 8–9 (1992) —1.4.
Stüber W. et al.—Peptide Research—vol. 8, No. 2, pp. 78–85 (1995).

*Primary Examiner*—Sandy Saucier
*Attorney, Agent, or Firm*—Stephen L. Nesbitt

[57] ABSTRACT

The present invention is related to a novel process for preparing N-acetyl-(L)-4-cyanophenylalanine by resolving the racemic compound N-acetyl-(D,L)-4-cyanophenylalanine ethyl ester, and a novel process to prepare a stereoisomer of Ac-(L)-pAph-Chg-PalMe(3)-NH₂ by using the intermediate N-acetyl-(L)-4-cyanophenylalanine.

28 Claims, No Drawings

PROCESS FOR PREPARING N-ACETYL(L)-4-CYANOPHENYLALANINE FROM A MIXTURE OF THE CORRESPONDING D,L ETHYL ESTERS USING SUBTILISIN

This application claims the benefit of U.S. Provisional application Ser. No. 60/080,231, filed Dec. 20, 1995.

FIELD OF THE INVENTION

The present invention is related to a novel process for preparing N-acetyl-(L)-4-cyanophenylalanine by resolving the racemic compound N-acetyl-(D,L)-4-cyanophenylalanine ethyl ester, and a novel process to prepare a stereoisomer of Ac-(L)-pAph-Chg-PalMe(3)-NH$_2$ by using the intermediate N-acetyl-(L)-4-cyanophenylalanine.

BACKGROUND OF THE INVENTION

The racemic compounds N-acetyl-(D,L)-4-cyanophenylalanine and Ac-(L)-pAph-Chg-PalMe(3)-NH$_2$ are disclosed and described in Ser. No. 08/428,404, filed Apr. 25, 1995, which is a continuation-in-part of U.S. Ser. No. 08/233,054, filed Apr. 26, 1994 and which is herein incorporated by reference. The end product Ac-(L)-pAph-Chg-PalMe(3)-NH$_2$ is useful as an inhibitor of Factor Xa.

It is desirable to have stereoisomers to develop as drugs rather than racemates since the stereoisomers may possess advantages over the racemates such as superior efficacy, less side effects, lower levels or absence of toxicity, etc. Sometimes these advantages of the stereoisomer over the racemate are not known until late in the development of the drug or sometimes not even until the drug has been marketed. It is also preferred by many governmental agencies which approve drugs for the market to approve a dossier on the stereoisomer of the drug rather than the racemate. Therefore, it was desirable to have a process for making a stereoisomer of the compound Ac-(L)-pAph-Chg-PalMe(3)-NH$_2$. A key intermediate for producing this stereoisomer is the stereoisomer N-acetyl-(L)-4-cyanophenylalanine.

In order to resolve a racemate one must select from the variety of technics known for this purpose. Some examples are the formation of diastereomers followed by crystallization or differential absorption (chromatography) [as described in *Enantiomers, Racemates, and Resolutions*, J. Jacques, A. Collet, and S. H. Wilen, Wiley (1981)], chromatographic separation on chiral stationary phase, kinetic resolution, and enzymatic resolution. Enzymatic resolution, in particular hydrolases or esterases, have proved to be useful in the resolution of amino acids as described in *Chemistry and Biochemistry of the amino acids*, Chapman and Hall, New York, 1984, Chap. 10 pp. 338–353; in *Applications of Biochemical Systems in Organic Chemistry*, Part I, J. B. Jones, C. J. Sih, and D. Perlman, Wiley, New York, 1976, Chap 4. pp. 107–401; and in *Chemistry of the Amino Acids*, vol.1. Wiley, New York, 1961, Chap 9. pp 728–750.

Even after a process is chosen, one skilled in the art must then extensively experiment to find the right solvent, co-solvent (if necessary), temperature, time, and other conditions to provide an effective and efficient resolution of the racemate which provides easy recovery of the compound of interest, high yields, high enantiomeric excess, and a process not too difficult to perform. The present invention solves these problems for the resolution of N-acetyl-(D,L)-4-cyanophenylalanine, the L isomer of which is then used as an intermediate in the production of of Ac-(L)-pAph-Chg-PalMe(3)-NH$_2$, compound (II).

SUMMARY OF THE INVENTION

The invention provides a process for preparing N-acetyl-(L)-4-cyanophenylalanine, compound (IA):

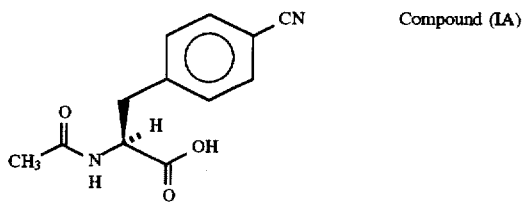
Compound (IA)

comprising the steps of:
a) combining a sufficient amount of compound (I):

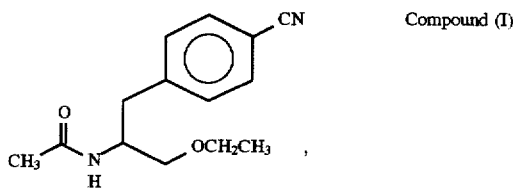
Compound (I)

a sufficient amount of an aqueous solution, a sufficient amount of acetonitrile, and a sufficient amount of subtilisin to react with a substantial amount of the compound (I) to form a reaction medium; and b) adjusting the reaction medium to an appropriate pH when the subtilisin is added and maintaining the appropriate pH while a reaction occurs to produce the compound (IA).

The invention further provides a process for preparing compound Ac-(L)-pAph-Chg-PalMe(3)-NH$_2$, Compound (II):

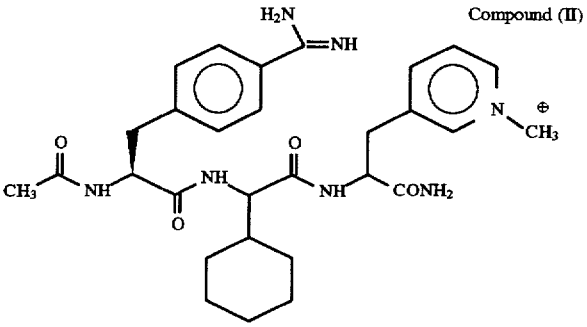
Compound (II)

or pharmaceutically acceptable salts thereof, comprising the steps of:
a) combining a sufficient amount of compound (I):

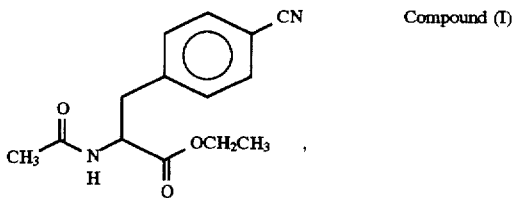
Compound (I)

a sufficient amount of an aqueous solution, a sufficient amount of acetonitrile, and a sufficient amount of subtilisin to react with a substantial amount of the compound (I) to form a reaction medium; and b) adjusting the reaction medium to an appropriate pH when the subtilisin is added and maintaining the appropriate pH while a reaction occurs to produce the compound (IA):

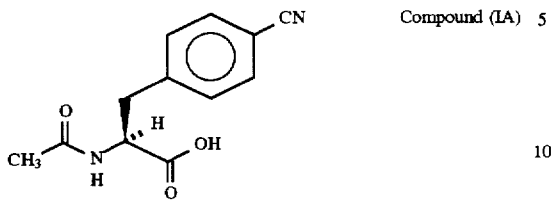

Compound (IA)

c) coupling the compound (IA) with compound (3):

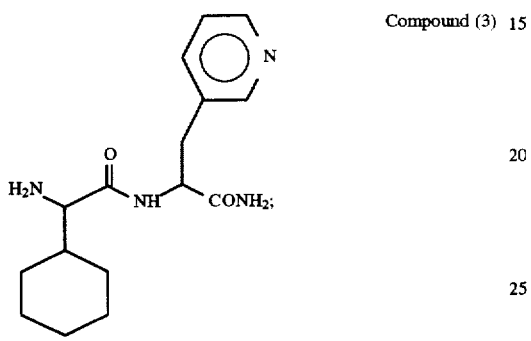

Compound (3)

to give compound (4);

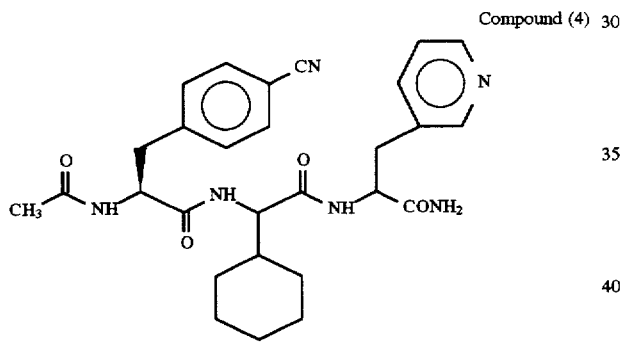

Compound (4)

d) converting the cyano group of compound (4) into the amidino group and methylating the nitrogen of the pyridyl group to give compound (II).

DETAILED DESCRIPTION OF THE PREFERRED EMBODIMENTS

The following terms have the meaning described hereafter:

(a) the term "Ac" or "acetyl" refers to a functionality of the formula:

$$CH_3-\overset{O}{\underset{\|}{C}}-;$$

(b) the term "Amidino" refers to a functionality of the formula:

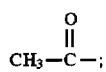

(c) the term "pyridyl" refers to a functionality of the formula:

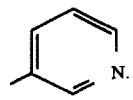

Stereoisomers is a general term for all isomers that differ only in the orientation of their atoms in space. It includes isomers of compounds with more than one chiral center that are not mirror images of one another (diastereomers or diastereoisomers). The term "enantiomer" refers to two stereoisomers that are non superimposable mirror images of one another. The term "chiral center" refers to a carbon atom to which four different groups are attached. The nomenclature L/D or R/S is used as described in IUPAC-IUB Joint Commission on Biochemical Nomenclature, *Eur. J. Biochem.* 138: 9–37 (1984). A chiral material may either contain an equal amount of the R and S isomers (or L and D isomers) in which case it is called "racemic" or "a racemate" or it may not contain equal amounts of R and S (or L and D isomers) in which case it is called "optically active" or "nonracemic".

The term "resolution" means separation of a racemic mixture into its optically active components.

The term "enantiomeric excess" or "ee" refers to the percent by which one enantiomer, E1, is in excess in a mixture of the two enantiomers, E1 plus E2, such that $$\frac{(E1-E2)}{(E1+E2)} \times 100\% = ee$$

The term (+)- refers to the plus enantiomer, (−)- refers to the minus enantiomer.

The designation "—■" refers to a bond that protrudes forward out of the plane of the page.

The designation "⋯⋯" refers to a bond that protrudes backward out of the plane of the page.

The term "pharmaceutically acceptable salts" include those acid addition salts derived by reaction with acids, for example, hydrochloric, hydrobromic, sulfuric, nitric or phosphoric acids and such organic carboxylic acids as acetic, trifluoroacetic, propionic, glycolic, maleic, tartaric, citric, salicylic, 2-acetyloxybenzoic acids or organic sulfonic acids such as methanesulfonic, 4-toluenesulfonic and naphthalenesulfonic acids. Of course other acids well known to the pharmaceutical art may also be utilized.

As used herein the term "amino acid" is meant to include the naturally occurring amino acids which are translated from the genetic code and comprise the building blocks of the proteins. The term amino acid also intends to include, unless specifically stated otherwise both (L)-amino acids, (D)-amino acids, chemically modified amino acids such as amino acid analogs, naturally occurring amino acids which are not usually incorporated into proteins. Abbreviations of amino acids, amino acid analogs included within the scope of the specification are set forth in Table 1.

TABLE 1

| AMINO ACID | SYMBOL |
|---|---|
| Alanine | Ala |
| Phenylalanine | Phe |
| p-Cyanophenylalanine | Phe(4-CN) |
| p-Amidinophenylalanine | pAphe |
| Cyclohexylglycine | Chg |
| β-(3-pyridyl)-alanine | Pal |

TABLE 1-continued

| AMINO ACID | SYMBOL |
|---|---|
| β-(3-N-methylpyridinium)-alanine | PalMe(3) |

SCHEME 1: RESOLUTION OF COMPOUND (I)
Scheme 1: Resolution of N-Acetyl-(D,L)-4-cyanophenylalanine ethyl ester

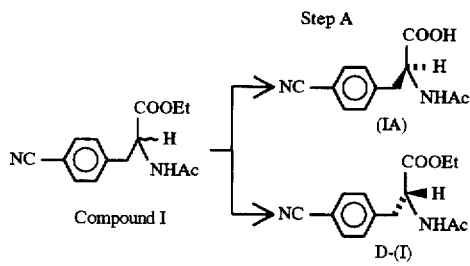

The racemate of the ethyl ester (compound (I)) is resolved to the L stereoisomer of the acid N-acetyl-4-cyanophenylalanine (compound (IA)) whereas the D stereoisomer of the ester (compound D-(I)) is not substantially converted into the acid. Thus separation of the desired acid from the unwanted ester can be performed. As more fully described hereafter, the acid obtained by this process is primarily the L isomer as shown by its high ee factor.

The sufficient amount of compound (I) combined to form the reaction medium is at least twice as much as is desired to be recovered as the L stereoisomer by the method of the present invention. The reaction medium comprises a sufficient amount of acetonitrile and a sufficient amount of an aqueous solution. These sufficient amounts are required to permit the additives to interact according to the method of the present invention. As used herein, "additives" mean anything added to the reaction medium.

A sufficient amount of acetonitrile would be an amount which solubilizes a substantial amount of compound (I) in the reaction medium. Preferably compound (I) is solubilized into acetonitrile and the aqueous solution is added slowly till just before the aqueous solution becomes cloudy. The cloudy solution indicates that a part of compound (I) precipitated, therefore an additional amount of acetonitrile may be required to dissolve the precipitate. For example, a sufficient amount of acetonitrile is from about 5 to 95% by volume of the reaction medium and more preferably from about 50 to 60% by volume. Preferably compound (I) is in concentration from about 20 g to 140 g per liter of reaction medium and more preferably from about 35 g to 65 g per liter.

A sufficient amount of an aqueous solution would be an amount which solubilizes a substantial amount of the enzyme Subtilisin in the reaction medium. As used herein, "aqueous solution" is a solution comprising water, and more preferably, water and other additives which assist in the enhancement of the yield or ee factor. The term "solution" does not necessarily mean that any additive added to the aqueous solution is dissolved; it can also mean that additives are dispersed so that there is a suspension.

For example, the aqueous solution may further comprise as an additive a sufficient amount of an inorganic salt such as potassium chloride, sodium chloride, lithium chloride, etc.. Preferably, the inorganic salt is potassium chloride. It is believed that the inorganic salt functions to stabilize the Subtilisin. A sufficient amount of inorganic salt is an amount which would be enough to stabilize the subtilisin. This is about 0.02 mol to about 0.20 mol per liter of aqueous solution, more preferably about to 0.05 to 0.15 mol per liter. For example, a solution of potassium chloride 1M is combined in a range of about 10 to about 15 percent in volume of the reaction medium.

Combined with compound (I), acetonitrile and the aqueous solution is a sufficient amount of the Subtilisin. A sufficient amount of the subtilisin is an amount capable of reacting with a substantial amount (practically all if possible) of compound (I). This is about 0.5 to about 10 milliequivalent by weight of the amount of compound (I).

The pH of the reaction medium is measured when the enzyme is added and, if necessary, adjusted to an appropriate pH. An appropriate pH is pH for which the enzyme is capable of reacting. Preferably the appropriate pH is from about 5 to about 9, and more preferably from about 6.5 to about 7.5. The appropriate pH is maintained while the reaction between compound (I) and the subtilisin occurs. This is about 15 minutes to 4 hours, preferably with agitation or other appropriate method to aid in the reaction. Any appropriate means may be used to maintain the appropriate pH, e.g., by adding a sufficient amount of a base such as sodium hydroxide, potassium hydroxide, lithium hydroxide, ammonium hydroxide, sodium carbonate, potassium carbonate, preferably in a 1M solution or by adding a buffer solution such as for example ammonium acetate, ammonium bicarbonate, sodium bicarbonate or a phosphate buffer such as ammonium hydrogenophosphate, sodium hydrogenophosphate. A pH meter may be used to monitor the pH of the reaction medium.

Compound (IA) may be collected according to well known methods in the art such as for example, the solution is diluted by addition of a basic solution of an inorganic salt such as for example sodium bicarbonate. The inorganic phase is washed by organic solvents such as for example ethers, chlorinated solvents such as methylene chloride, chloroform, toluene, heptane or ethyl acetate. The aqueous solution is acidified using a concentrated acid such as for example hydrochloric acid to a pH from about 1 to 3 and extracted with organic solvent to give compound (IA).

Table 2 and table 3

Table 2 and table 3 give comparison of reactions run with an aqueous solution and acetonitrile (table 2); and with an aqueous solution and dimethyl sulfoxide instead of acetonitrile (table 3).

Column A gives the quantity in grams of compound (I) used in the assay.

Column B gives the quantity in millimeters (mL) of dimethyl sulfoxide (DMSO) or acetonitrile ($CH_3CN$), of water and of a solution of potassium chloride 1M used to prepare the aqueous solution.

Column C gives the quantity of the Subtilisin in milligrams (mg) used and the corresponding milliequivalent (meq) in weight of compound I.

Column D gives the time for running the experiment.

Column E gives the enantiomeric excess of compound (IA) obtained.

Column F gives the yield of compound (IA) obtained.

TABLE 2

In entry 1 the reaction was run in presence of an inorganic salt (potassium chloride). In entry 2 the reaction was run without the inorganic salt.

| | | Column | | | | |
|---|---|---|---|---|---|---|
| Entry | A (I) (D:L; 60:40) (g) | B CH₃CN/H₂O/ 1M KCl (mL) | C Subtilisin (mg) (meq) | D Time (min) | E (IA) % ee | F (IA) % yield |
| 1 | 67 | 1000/600/214 | 100 (3.7) | 180 | 99.4 | 88 (solid)[3] |
| 2 | 1 | 15/9.5/0 | 01.6 (3.2) | 120 | 98 | 90 (solid)[3] |

TABLE 3

The reactions using dimethyl sulfoxide were run in various conditions differing in time, proportion of the Subtilisin, quantity of compound (I).

| | | | Column | | | |
|---|---|---|---|---|---|---|
| Entry | A (I) (g) | B DMSO/H₂O/ 1M KCl (mL) | C Subtilisin (mg) (meq) | D Time (min) | E (IA) % ee | F (IA) % yield |
| 1 | 2.0 | 32/18/6.4 | 1.5 (1.5) | 30 | 95.4 | 70 (oil in DMSO)[1] |
| 2 | 7.8 | 125/100/25 | 12 (3.0) | 30 | 94 | 88 (oil, DMSO)[1] |
| 3 | 25 | 400/200/81 | 19 (1.5) | 40 | 88 | 70 (oil in DMSO)[1] |
| 4 | 100 | 1600/900/320 | 75 (1.5) | 60 | 88 | 90 (oil in DMSO)[1] |
| 5 | 2.8 | 10/8/2 | 4.4 (3.0) | 65 | 86 | 50 (solid)[2] |
| 6 | 2.0 | 42/26/6.4 | 1.5 (1.5) | 120 | 80 | 70 (oil in DMSO)[1] |

[1] DMSO present in compound (IA), very difficult to remove.
[2] Removal of DMSO by evaporation at 90° C./8 torr, dissolution into ethyl acetate and wash with water (3×).
[3] Compound (IA) is easily isolated as a solid.

These tests show the effective and efficient resolution with easy recovery of compound (IA), with high yields and high enantiomeric excess when acetonitrile is used.

Scheme 2

Scheme 2 is a continuation of Scheme 1 and gives a process for preparing compound Ac-(L)-pAph-Chg-PalMe(3)-NH₂, compound (II).

In Scheme 2, step A, compound (3) is coupled with compound (IA) to give compound (4). Compound (3) may be coupled using an azide method such as for example, compound (IA) is dissolved in a suitable anhydrous organic solvent, such as anhydrous dimethylformamide or anhydrous methylene chloride under an inert atmosphere, such as nitrogen. To this solution is added diphenylphosphorylazide, 1 to 4 equivalents of a suitable base such as diisopropyl ethyl amine and at least one equivalent of the protected amino acid, compound (3), dissolved in a suitable anhydrous organic solvent, such as anhydrous dimethylformamide or anhydrous methylene chloride. The reaction is then allowed to stir for about 1 to 15 hours. The coupled product (4) is then isolated and purified by techniques well known in the art, such as extractive techniques, precipitation, crystallization and flash chromatography. For example, solvents are evaporated, coupled product (4) is precipitated by ethyl ether, washed and collected by filtration.

In scheme 2, steps B and D, the cyano group of compound (4) is converted to the amidino group of compound (II). This conversion is accomplished by aminolysis of the corresponding methylthioimidate of compound (5) (formed by reaction of the cyano group of compound (4) with hydrogen sulfide) following the procedure given by Wagner et al., DDR Patent No. 155,954, issued 21, 1982; reexamined Nov. 9, 1988, which is herein incorporated by reference.

For example, in scheme 2, step B, compound (4) is dissolved in an organic solvent such as dimethyl sulfoxide. Organic bases such as for example pyridine, triethylamine diisopropylethylamine, 2,6-lutidine, collidine are added. A stream of hydrogen sulfide is passed through the solution at room temperature until compound (4) is consumed. The reaction may be kept at room temperature for an additional time from 1 to 18 hours. Compound (5) is collected according to well known method in the art such as by precipitation and filtration. The precipitate is then washed by an organic solvent such as diethyl ether and dried under vacuo.

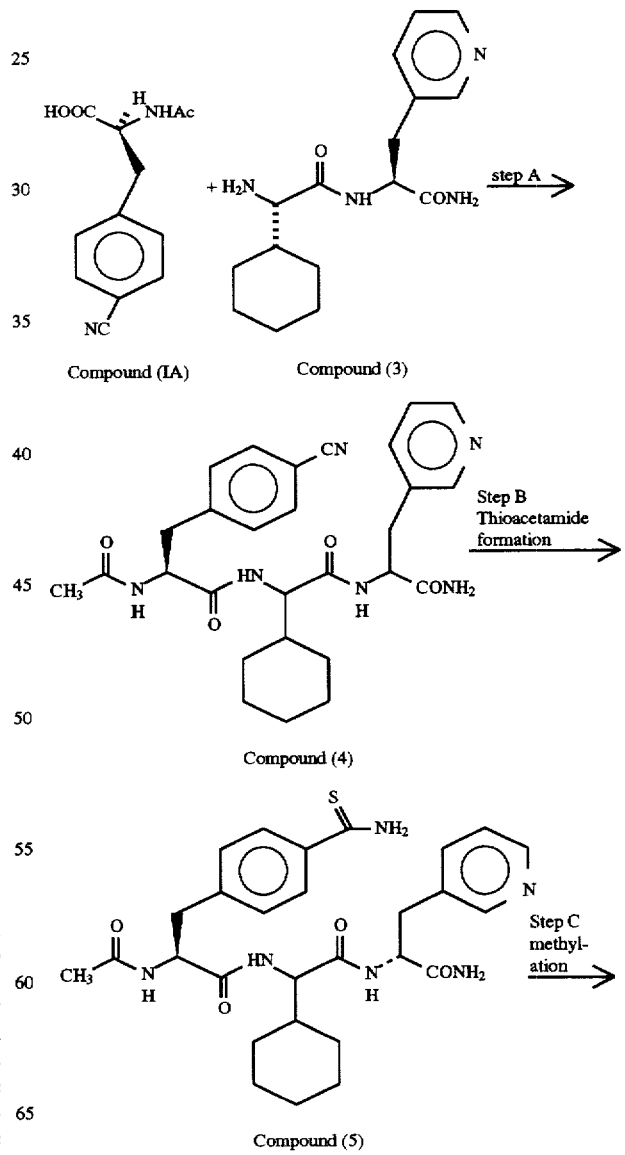

Scheme 2: Synthesis of Ac—(L)—pAph—Chg—Pal—Me(3)—NH₂

-continued
Scheme 2: Synthesis of Ac—(L)—pAph—Chg—Pal—Me(3)—NH₂

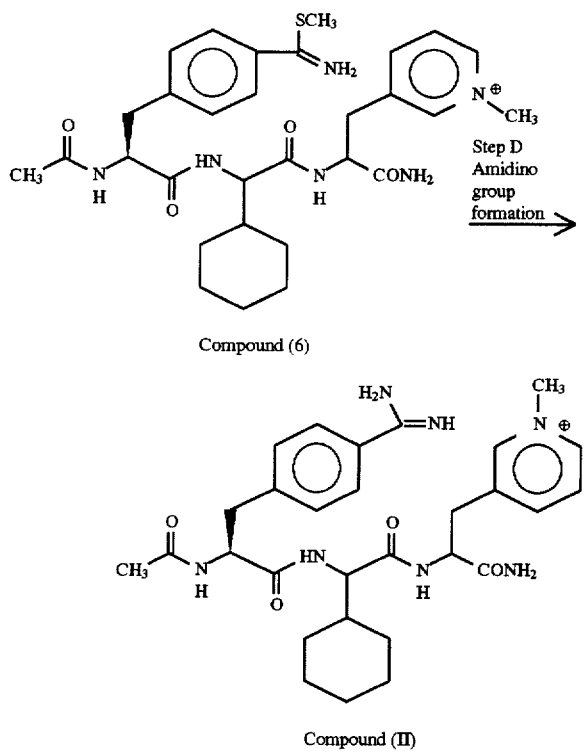

Compound (6)

Compound (II)

In scheme 2, step C, the pyridyl group of compound (5) is methylated to give compound (6). More commonly for the methylation, methyl halides such as methyl iodide, methyl bromide or methyl chloride may be used. Methyl fluorosulfonate, dimethyl sulfate, methyl toluene-p-sulfonate and other methylating agents such as disclosed by Zoltewicz and Deady, Adv. Heterocycl. Chem. 22, 71–121 (1978), and by Duffin, Adv. Heterocycl. Chem. 3, 1–56 (1964) which are herein incorporated by reference, may be used too. Preferably an excess of methyl halides is used and more preferably an excess of methyl iodide. The reaction is carried out in solvents such as alcohols such as for example methanol and ethanol, acetone, chloroform, acetonitrile, nitrobenzene and dimethylformamide. More preferably the reaction is performed in a mixture of acetone and dimethylsulfoxide and agitated at room temperature from one to 24 hours. Compound (6) is isolated according to well known procedures in the art such as the excess of methyl iodide is evaporated and compound (6) is precipitated by ethyl ether, collected by decantation, washed and dried.

In scheme 2, step D, the methylthioimidate of compound (6) is further converted into its corresponding amidino group of compound (II). Preferably, compound (6) is dissolved in organic solvent such as methanol, more preferably in presence of acetic acid. Ammonium acetate is added to the solution. Preferably, the reaction is heated at a range of temperature from 40° C. to 65° C., more preferably in a range from 50° C. to 60° C. and kept at this temperature from 2 to 3 hours. Compound (II) is isolated according to well known procedure in the art and may be isolated as a pharmaceutically acceptable salt. For example, the solvents are evaporated, the residue may be dissolved in acetonitrile and precipitate by addition of trifluoroacetic acid, filtered and dried under vacuo.

The following examples present typical syntheses as described in scheme 1 and scheme 2. These examples are understood to be illustrative and are not intended to limit the scope of the invention in any way.

As it is appreciated to one skilled in the art, in schemes the order in which the steps are carried out may be optional.

Starting materials are commercially available or easily prepared by well known procedures in the art.

As used herein, the following terms have the indicated meanings: "g" refers to grams; "mol" refers to moles; "mmol" refers to millimoles; "L" refers to liters; "mL" refers to milliliters; "µL" refers to microliters; "mp" refers to melting point; "°C." refers to degrees Celsius; "TLC" refers to thin layer chromatography; "M" refers to molarity; and "Rf" refers to retention factor.

EXAMPLE 1

(D,L)-N-ACETYL-4-CYANOPHENYLALANINE
Ac-(D,L)-Phe(4-CN)-OH

Step A: Diethyl 4-cyanobenzylacetamidomalonate

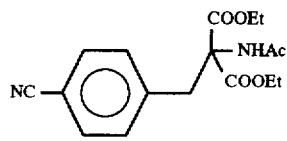

Suspend diethylacetamidomalonate (44 g, 0.203 mol), alpha-bromo-p-toluonitrile (40 g, 0.204 mol), potassium iodide (10 g) in dioxane (400 mL) and add a solution of sodium ethoxide (4.6 g of sodium in 200 mL of dry ethanol). Heat under reflux the mixture for 3–4 hours and let stay overnight. Pour the mixture on ice (2 L), filtrate the precipitate, wash with water and dry on lyophyliser. Recrystallize from methanol, to give diethyl 4-cyanobenzylacetamidomalonate as white crystals (61 g, 91%).

Step B: N-(D,L)-acetyl-4-cyanophenylalanine ethyl ester, Ac-(D,L)Phe(4-CN)-OEt

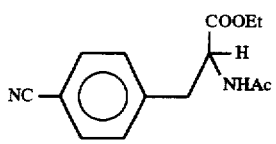

Suspend 4-cyanobenzyl diethylacetamidomalonate (41.97 g 0.126 mol) in ethanol (0.6 L). Add sodium hydroxide (6M) in the following intervals: 10 mL (60 mmol) at 0 minute, 10 mL (60 mmol) after 30 minutes, 3 h 5 mL (30 mmol) after 3 hours. Stir the reaction with addition of sodium hydroxide (6M) until the starting material disappears (TLC, ethyl acetate, Rf=0.63). Dilute the solution with water (100 mL) and adjust pH by addition of concentrate hydrochloric acid to 3. Evaporate ethanol an dry the semisolid product on lyophyliser overnight to give the N-acetyl-4-cyanobenzyl monoethyl acetamidomalonate.

Suspend the so-produced N-acetyl-4-cyanobenzyl monoethyl acetamidomalonate in dry dioxane (0.5 L) and heat under reflux for 2.5–3 hours. Evaporate dioxane, suspend solid in ethyl acetate (250 mL) and extract with a saturated aqueous solution of saturated sodium bicarbonate (3x), water, hydrochloric acid (0.5M), and brine. Dry the ethyl acetate solution on magnesium sulfate, filtrate and evaporate. Recrystallize the product from ethyl acetate/hexanes to give 28.95 (88%) of N-(L,D)-acetyl-4-cyanophenylalanine ethyl ester.

EXAMPLE 2

Enzymatic resolution of Ac-(D,L)Phe(4-CN)-OEt (6:4; D:L) and preparation of (L)-N-acetyl-4-cyanophenylalanine, Ac-(L)Phe(4-CN)-OH

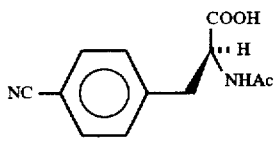

Add potassium chloride solution (1M, 241 mL) and water (600 mL) to a solution of Ac-(D,L)Phe(4-CN)-OEt (6:4; D:L, 67 g) in acetonitrile (1L). Adjust the pH of the solution from 7.3 to 6.9 and add a solution of subtilisin Carlsberg (50 mg) in aqueous potassium chloride (8 mL, 0.1M). Maintain the pH of the solution by titrating with sodium hydroxide (1M). After one hour add a solution of subtilisin (50 mg) in aqueous potassium chloride (8 mL, 0.1M) and maintain the pH of the solution by titrating with sodium hydroxide (1M). After 2.5 hours add a solution sodium bicarbonate (800 mL) and extract with ethyl acetate (4×800 mL). Dry the ethyl acetate solution on magnesium sulfate and filtrate the mixture. Concentrate the filtrate to give Ac-(D)Phe(4-CN)-OEt as a solid (38 g, 95%, 90% ee). Acidify the aqueous layer concentrated hydrochloric acid (56 mL) to pH 1. Extract the aqueous layer with ethyl acetate (4×800 mL). Dry the organic layer on magnesium sulfate and filtrate the mixture. Concentrate the filtrate to give Ac-(L)Phe(4-CN)-OH as a solid (21 g, 88%). mp 124°–126° C. 99.4% ee

EXAMPLE 3

N-Acetyl-(L)-p-amidinophenylalanine, Ac-(L)-pAph-(L)-Chg-(L)-PalMe(3)-NH₂

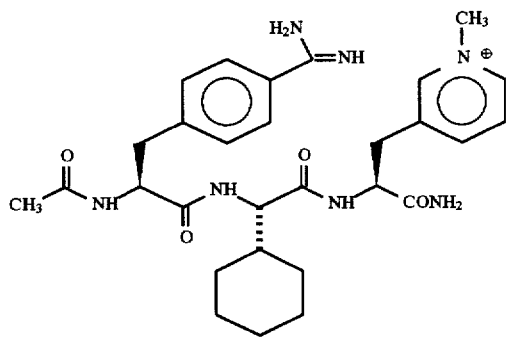

Step A: N-t-butyloxycarbonyl-(L)-β-(3-pyridyl)-alanine amide, Boc-(L)-Pal-NH₂

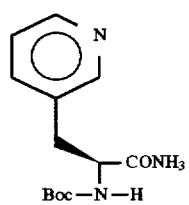

Suspend Boc-(L)-Pal-OH (1.34 g, 5 mmol) in methylene chloride (50 mL) and cool to −15° C. Add diisopropylethylamine (963 μl, 5.5 mmol) and isobutylchloroformate (715 μL, 5.5 mmol). Stir the mixture 15 minutes at −15° C. Pass through the solution a vigorous stream of anhydrous ammonia (over solid sodium hydroxide) for about 3 minutes. Stir the mixture 10 minutes at −15° C. and 20 minutes at room temperature. Evaporate methylene chloride, add ethyl acetate (70 mL) and wash with saturated aqueous solution of sodium bicarbonate. Dry over magnesium sulfate and evaporate. Crystallize from ethyl acetate/hexane to give Boc-(L)-Pal-NH₂ (0.98 g, 75%).

Step B: (L)-β-(3-pyridyl)-alanine amide hydrochloric acid salt, H-(L)-Pal-NH₂. 2HCl

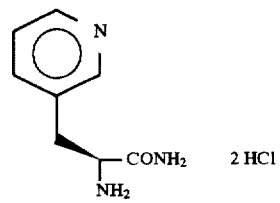

Suspend Boc-(L)-Pal-NH₂ (0.98 g) in methylene chloride (15 mL) with light heating and add a solution of hydrochloric acid (4M, 10 mL) in dioxane. After 30 minutes evaporate methylene chloride and dioxane. Dissolve the solid in methanol, precipitate by addition of ether and filtrate to give H-(L)-Pal-NH₂. 2HCl (0.86 g, 98%).

Step C: N-t-butyloxycarbonyl-(L)-cyclohexylglycine-(L)-β-(3-pyridyl)-alanine amide Boc-(L)-Chg-(L)-Pal-NH₂

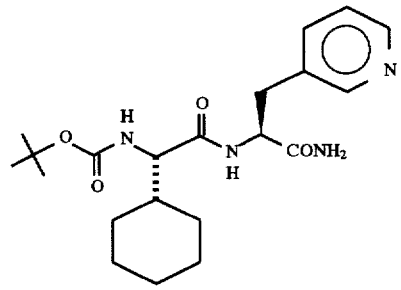

Stir overnight H-(L)-Pal-NH₂.2HCl (432 mg, 1.82 mmol), Boc-(L)-Chg-OH (609 mg, 2.37 mmol, 1.3 equivalent), dicyclohexylcarbodiimide (494 mg, 2.4 mmol), hydroxybenzotriazole (324 mg, 2.4 mmol) and diisopropylethylamine (4 mmol) in dimethyl formamide (15 mL). Evaporate dimethyl formamide, add ethyl acetate and store the mixture at room temperature for 1 h. Filter off the diisopropylcarbodiimidecyclohexylurea formed, extract the solution by a saturated solution of sodium bicarbonate (3×), dry over magnesium sulfate, and evaporate. Crystallize by addition of hexanes to give Boc-(L)-Chg-(L)-Pal-NH₂ (598 mg, 81%).

Step D: (L)-cyclohexylglycine-(L)-β-(3-pyridyl)-alanine amide hydrochloric acid salt H-(L)-Chg-(L)-Pal-NH₂.2HCl

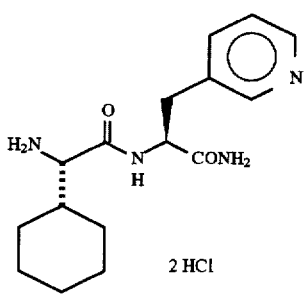

Suspend Boc-(L)-Chg-(L)-Pal-NH₂ (1.27 g, 3.12 mmol) in methylene chloride (50 mL), and add chlorhydric acid (10 mL, 4M in dioxane). After 30 minutes, evaporate dioxane and methylene chloride, dissolve the solid in methanol and precipitate the product by addition of ether (200 mL) and filter to give H-(L)-Chg-(L)-Pal-NH₂.2HCl (1.12 g, 95%).

Step E: N-Acetyl-p-cyanophenylalanine-(L)-cyclohexylglycine-(L)-β-(3-pyridyl)-alanine amide Ac-(L)-Phe(4-CN)-(L)-Chg-(L)-Pal-NH₂

Stir overnight H-(L)-Chg-(L)-Pal-NH₂.2HCl (1.13 g, 3 mmol), Ac-(L)Phe(4-CN)-OH (0.84 g, 3.6 mmol), diisopropylethylamine (10 mmol), and diphenylphoshoryl azide (803 μl 3.6 mmol) dimethyl formamide (30 mL) overnight. Evaporate dimethyl formamide, precipitate by ether, filter and wash by ether to give Ac-(L)-Phe(4-CN)-(L)-Chg-(L)-Pal-NH₂ (1.282 g, 82%).

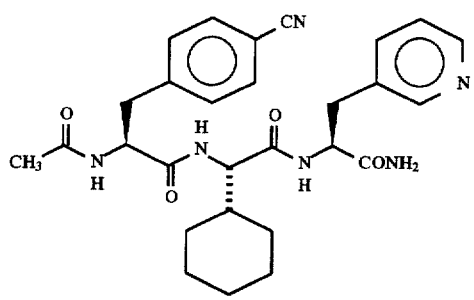

Step F: N-Acetyl-(L)-p-thioamidephenylalanine-(L)-cyclohexylglycine-(L)-β-(3-pyridyl)-alanine amide Ac-(L)-Phe(4-thioamide)-(L)-Chg-(L)-Pal-NH₂

Dissolve of Ac-(L)-Phe(4-CN)-(L)-Chg-(L)-Pal-NH₂ (1.18 g, 2.28 mmol) in dimethyl sulfoxide (20–40 mL) and add pyridine (40 mL) and triethylamine (14 mL). Pass hydrogen sulfide through the solution at room temperature for 30 minutes. Keep the solution overnight at room temperature, evaporate to small volume and precipitate the product by diethyl ether. Keep in refrigerator for several hours, filter, wash by diethyl ether and dry in vacuo to give Ac-(L)-Phe(4-thioamide)-(L)-Chg-(L)-Pal-NH₂ (1.26 g) as a yellow solid.

Step G: N-Acetyl-p-methylthioamidatephenylalaninecyclohexylglycine-(L)-β-(3-methylpyridinium)-alanine hydroiodide acid salt Ac-(L)-Phe(4-methyl thioamidate)-(L)-Chg-(L)-Pal(Me)-NH₂.2HI

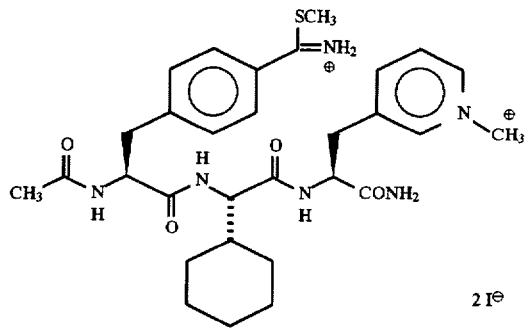

Suspend Ac-(L)-Phe(4-thioamide)-(L)-Chg-(L)-Pal-NH₂ (1.2 g) in dimethyl sulfoxide (10–20 mL) and acetone (80 mL). Add methyl iodide (14 mL, 50 equivalents). Keep the reaction overnight at room temperature, evaporate the acetone and excess of methyl iodide. Precipitate by diethyl ether (0.5–1.1). After several hours at 4° C., decant or filter diethyl ether and the semisolid on walls is washed by diethyl ether and ethyl acetate. Dry the product in vaccuo to give Ac-(L)-Phe(4-methyl thioamidate)-(L)-Chg-(L)-Pal(Me)-NH₂.2HI (1.31 g).

Step H: N-Acetyl-(L)-p-acetamidophenylalaninecyclohexylglycine-(L)-β-(3-N-methylpyridinium)-alanine amide trifluoroacetic acid salt Ac-(L)-pAphe-(L)-Chg-(L)-PalMe-NH₂ TFA Dissolve of Ac-(L)-Phe(4-methyl thioamidate)-(L)-Chg-(L)-Pal(Me)-NH₂.2HI (1.31 g) in methanol (50 mL) and acetic acid (0.5 mL). Add ammonium acetate (0.8 g). Heat the mixture to 55° C. for 3 hours, evaporate, dissolve in acetonitrile/water (0.1% trifluoroacetic acid) (1:1), filter and lyophilize to give Ac-(L)-pAphe-(L)-Chg-(L)-PalMe-NH₂.TFA (1.22 g).

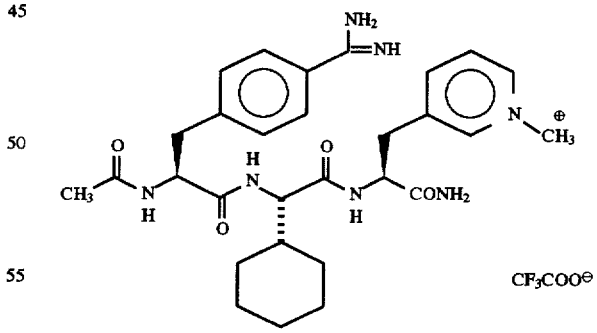

The present invention relates to the preparation of the intermediate N-acetyl-L-phenylalanine compound (IA) useful in the preparation of Ac-(L)-pAph-Chg-PalMe(3)-NH₂, compound (II). This last compound is useful in the inhibition of blood clotting proteins, and more particularly, in in the inhibition of blood clotting enzyme factor "Xa" as more fully described in the U.S. application Ser. No. 08/428,404 filed Apr. 25, 1995 which is herein incorporated by reference.

As used herein, the term "factor Xa activity" refers to the ability of factor Xa, by itself or in the assembly of subunits known as the prothrombinase complex, to catalyze the conversion of prothrombin to thrombin. When used in reference to factor Xa activity, the term "inhibition" includes both the direct and the indirect inhibition of factor Xa activity. Direct inhibition of factor Xa activity can be accomplished, for example, by the binding of the peptide to factor Xa or to prothrombinase so as to prevent the binding of prothrombin to the prothrombinase complex active site.

As used herein, the term "specific" when used in reference to the inhibition of factor Xa activity is intended to mean that the compound inhibits factor Xa activity without substantially inhibiting the activity of other specified proteases (using the same concentration of the inhibitor). Such other specified proteases include, for example, those proteases involved in the coagulation cascade such as thrombin, plasmin, trypsin and elastase.

Although in certain disease states the formation of blood clots within the circulatory system is itself a source of morbidity, it is not desirable to completely inhibit the clotting system because life threatening hemorrhage would ensue.

The process of blood coagulation is a complex one, involving a progressively amplified series of enzyme activation reactions in which plasma zymogens are sequentially activated by limited proteolysis. Mechanistically the blood coagulation cascade has been divided into two pathways, "Intrinsic" and "Extrinsic". These pathways converge at the activation of factor X, with subsequent generation of thrombin proceeding through a single "common pathway".

Present evidence suggests that the intrinsic pathway plays an important role in the maintenance and growth of fibrin formation, while the extrinsic pathway is critical in the initiation phase of blood coagulation. It is now generally accepted that blood coagulation is physically initiated upon formation of a tissue factor/factor VIIa complex. Once formed, this complex rapidly initiates coagulation by activating factor IX and X. The newly generated Xa then forms a one-to-one complex with factor via and phospholipids. This so called prothrombinase complex is responsible for converting soluble fibrinogen to insoluble fibrin. As time progresses the activity of the factor VIIa/tissue factor complex (extrinsic pathway) is suppressed by a Kunitz-type protease inhibitor protein, TFPI, which, when complexed to factor Xa, can directly inhibit the proteolytic activity of factor VIIa/tissue factor. In order to maintain the coagulation process in the presence of an inhibited extrinsic system, additional factor Xa is produced via the thrombin-mediated activity of the intrinsic pathway. Thus thrombin plays a dual "autocatalytic" role mediating its own production and the conversion of fibrinogen to fibrin.

The autocatalytic nature of thrombin generation is an important safeguard against uncontrolled bleeding. It ensures that once a given threshold level of prothrombinase is present, blood coagulation will proceed to completion, effecting, for example, an end of the hemorrhage. Thus it is most desirable to develop agents which inhibit coagulation without directly inhibiting thrombin.

The compound Ac-pAph-Chg-PalMe(3)-NH$_2$, which is a peptide analog, synthesized via the the process of the present invention provides a useful inhibitor of factor Xa activity and does not substantially inhibit the activity of other proteases involved in the blood coagulation.

What is claimed is:

1. A process for preparing N-acetyl-(L)-4-cyanophenylalanine, compound (IA):

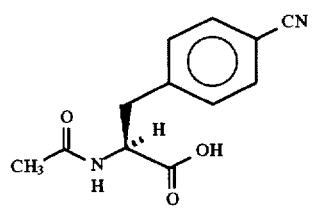

Compound (IA)

comprising the steps of:

a) combining a mixture of D,L enantiomers of compound (I):

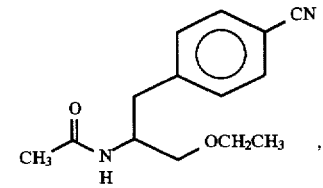

Compound (I)

with an amount of an aqueous solution sufficient to solubilize compound (I) in the reaction medium, and from 5–95% by volume of the reaction medium acetonitrile, and a sufficient amount of subtilisin to react with compound (I) to form a reaction medium; and b) adjusting the reaction medium to pH at which subtilisin is capable of reacting when the subtilisin is added and maintaining the pH while a reaction occurs to produce the compound (IA).

2. The process of claim 1 wherein the amount of acetonitrile is about 50 to about 60 percent by volume of the reaction medium.

3. The process of claim 1 wherein the aqueous solution further comprises an inorganic salt.

4. The process of claim 3 wherein the amount of the inorganic salt is about 10 to about 15 per cent by volume of the reaction medium of a 1 molar solution of the inorganic salt.

5. The process of claim 4 wherein the inorganic salt is potassium chloride.

6. The process of claim 1 wherein the pH of the reaction medium is adjusted and maintained by adding a sufficient amount of a base.

7. The process of claim 6 wherein the base is sodium hydroxide.

8. The process of claim 1 wherein the pH of the reaction medium is adjusted and maintained by the addition of a sufficient amount of a buffer.

9. The process of claim 8 wherein the buffer is a solution of phosphate.

10. The process of claim 1 wherein the pH of the reaction medium is adjusted and maintained at a pH from about 5 to about 9.

11. The process of claim 1 wherein the pH of the reaction medium is adjusted and maintained at a pH from about 6.5 to about 7.5.

12. The process of claim 1 further comprising agitating the reaction medium from about 15 minutes to about 4 hours while the reaction occurs between the subtilisin and compound (I).

13. The process of claim 1 wherein the subtilisin is from about 0.5 to about 10 milliequivalents by weight of the amount of Compound (I).

14. The process of claim 1 comprising a further step of collecting compound (IA) from the reaction medium.

15. A process for preparing Compound II:

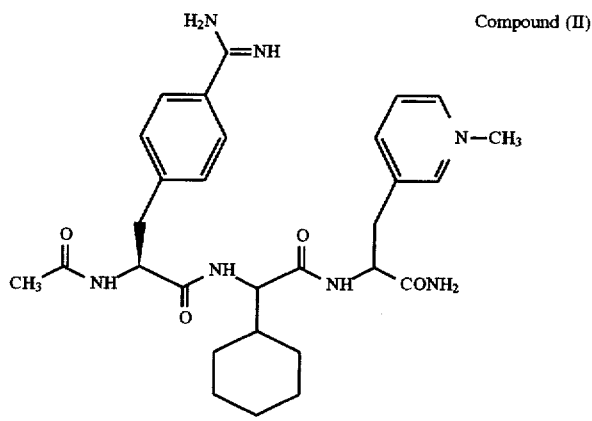
Compound (II)

or pharmaceutically acceptable salts thereof, comprising the steps of:

a) combining
 a mixture of D,L enantiomers of compound (I):

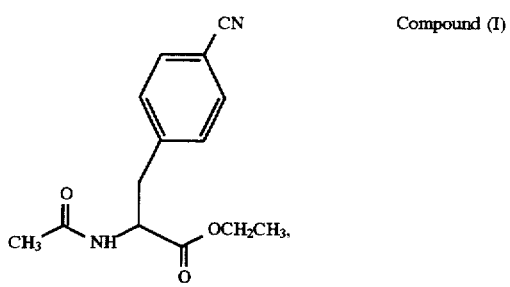
Compound (I)

with an amount of an aqueous solution sufficient to solubilize compound (I) in the reaction medium, and from 5–95% by volume of the reaction medium acetonitrile, and a sufficient amount of subtilisin to react with compound (I) to form a reaction medium; and b) adjusting the reaction medium to a pH at which subtilisin is capable of reacting when the subtilisin is added and maintaining the pH while a reaction occurs to produce the compound (IA):

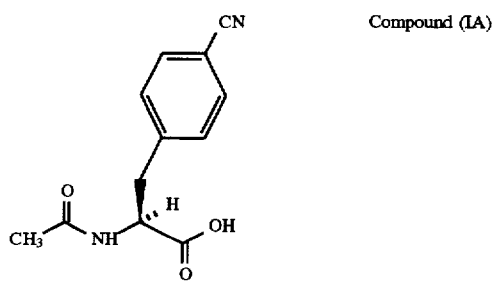
Compound (IA)

c) coupling the compound (IA) with compound (3):

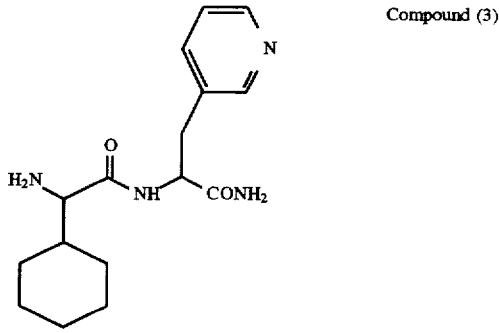
Compound (3)

to give compound (4):

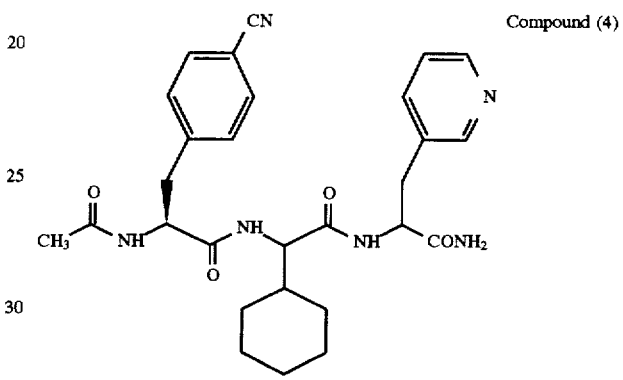
Compound (4)

d) converting the cyano group of compound (4) into the amidino group and methylating the nitrogen of the pyridyl group to give compound (II).

16. The process of claim 15 wherein the amount of acetonitrile is about 50 to about 60 percent by volume of the reaction medium.

17. The process of claim 15 wherein the reaction medium further comprises an inorganic salt.

18. The process of claim 17 wherein the amount of the inorganic salt is about 10 to about 15 per cent by volume of the reaction medium of a 1 molar solution of an inorganic salt.

19. The process of claim 18 wherein the inorganic salt is potassium chloride.

20. The process of claim 15 wherein the pH of the reaction medium is adjusted and maintained by adding a sufficient amount of a base.

21. The process of claim 20 wherein the base is sodium hydroxide.

22. The process of claim 15 wherein the pH of the reaction medium is adjusted and maintained by the addition of a sufficient amount of a buffer.

23. The process of claim 22 wherein the buffer is a solution of phosphate.

24. The process of claim 15 wherein the pH of the reaction medium is adjusted and maintained at a pH from about 5 to about 9.

25. The process of claim 15 wherein the pH of the reaction medium is adjusted and maintained at a pH from about 6.5 to about 7.5.

26. The process of claim 15 further comprising agitating the reaction medium from about 15 minutes to about 4 hours while the reaction occurs between the subtilisin and compound (I).

27. The process of claim 15 wherein the subtilisin is from about 0.5 to about 10 milliequivalents by weight to the amount of Compound (I).

28. The process of claim 15 comprising a further step of collecting compound (IA) from the reaction medium.

* * * * *